United States Patent
Colombo et al.

(10) Patent No.: US 10,813,888 B2
(45) Date of Patent: Oct. 27, 2020

(54) FORMULATIONS OF CYSTEAMINE AND CYSTEAMINE DERIVATIVES

(71) Applicant: RECORDATI INDUSTRIA CHIMICA E FARMACEUTICA SPA, Milan (IT)

(72) Inventors: Paolo Colombo, Parma (IT); Alessandra Rossi, Parma (IT); Greta Adorni, Noceto (IT); Marco Barchielli, Arese (IT)

(73) Assignee: RECORDATI INDUSTRIA CHIMICA E FARMACEUTICA SPA, Milan (MI) (IT)

( * ) Notice: Subject to any disclaimer, the term of this patent is extended or adjusted under 35 U.S.C. 154(b) by 0 days.

(21) Appl. No.: 16/332,840

(22) PCT Filed: Oct. 10, 2017

(86) PCT No.: PCT/EP2017/075801
§ 371 (c)(1),
(2) Date: Mar. 13, 2019

(87) PCT Pub. No.: WO2018/069313
PCT Pub. Date: Apr. 19, 2018

(65) Prior Publication Data
US 2019/0216741 A1    Jul. 18, 2019

(30) Foreign Application Priority Data
Oct. 11, 2016 (EP) .................................... 16193180

(51) Int. Cl.
*A61K 9/50* (2006.01)
*A61K 31/7024* (2006.01)
*A61K 9/16* (2006.01)
*A61K 31/145* (2006.01)
*A61K 9/00* (2006.01)
*A61P 25/28* (2006.01)

(52) U.S. Cl.
CPC .......... *A61K 9/5084* (2013.01); *A61K 9/0095* (2013.01); *A61K 9/167* (2013.01); *A61K 9/1617* (2013.01); *A61K 31/145* (2013.01); *A61K 31/7024* (2013.01); *A61P 25/28* (2018.01)

(58) Field of Classification Search
None
See application file for complete search history.

(56) References Cited

FOREIGN PATENT DOCUMENTS

| CN | 103652366 A | 3/2014 |
| WO | 0245693 A1 | 6/2002 |
| WO | 2007089670 A2 | 8/2007 |
| WO | 2010031785 A1 | 3/2010 |

(Continued)

OTHER PUBLICATIONS

Balducci et at, "Layered lipid microcapsules for mesalazine delayed-release in children", International Journal of Pharmaceutics, 2011, vol. 421, No. 2, pp. 293-300.

(Continued)

*Primary Examiner* — Kyung S Chang
(74) *Attorney, Agent, or Firm* — Lucas & Mercanti, LLP

(57) ABSTRACT

Oral cysteamine formulation consisting of dry layered lipid matrix microparticles useful for treating cystinosis and neurodegenerative disorders are described.

12 Claims, 6 Drawing Sheets

(56) References Cited

FOREIGN PATENT DOCUMENTS

WO          2014204881 A1     12/2014
WO      WO-2016005994 A2  *   1/2016   ........... A61K 9/2054

OTHER PUBLICATIONS

International Search Report and Written Opinion for Corresponding International Application No. PCT/EP2017/075801 (13 Pages) (dated Dec. 20, 2017).
Borella et al., "Sucralfate: antipeptic, antiulcer activities and antagonism of gastric emptying", Arznelmittelforschung, 1979, vol. 29, No. 5, English Abstract.

* cited by examiner

FORMULATIONS OF CYSTEAMINE AND CYSTEAMINE DERIVATIVES

CROSS-REFERENCE TO RELATED APPLICATIONS

This application is a 371 of PCT/EP2017/075801, filed Oct. 10, 2017, which claims the benefit of European Patent Application No. 16193180.3, filed Oct. 11, 2016.

FIELD OF THE INVENTION

The present invention relates to oral cysteamine formulations useful for treating cystinosis and neurodegenerative disorders and, in particular, to microparticle formulations containing cysteamine or cysteamine derivatives useful for treating cystinosis and neurodegenerative diseases such as Huntington, Alzheimer's and Parkinson's diseases.

BACKGROUND OF THE INVENTION

Cystinosis is an orphan, autosomal recessive disease causing an intra-lysosomal accumulation of the product cystine, a dimer of amino acid cysteine, within various tissues, including the spleen, liver, lymph nodes, kidney, bone marrow and eyes. Nephropathic cystinosis is associated with kidney failure that necessitates kidney transplantation. To date, the only specific treatment for nephropathic cystinosis is the mercaptamine drug, cysteamine. The use of cysteamine reducing the concentration of cystine levels in leucocytes has been shown to be effective in ameliorating the symptoms especially if the therapy begun at an early stage of the disease.

Cysteamine and its salts are unpalatable and may cause breath and body odor. In addition, cysteamine is ulcerogenic. When administered orally to children with cystinosis, cysteamine has been shown to cause an increase in gastric acid production and a rise of serum gastrin levels. As a consequence, subjects using cysteamine suffer for gastrointestinal symptoms and are often unable to continue to take cysteamine regularly.

To obtain a prolonged reduction of leukocyte cystine levels, patients are required to take oral cysteamine every 6 hours, which invariably means having to awake from sleep. The maintenance dose is 2 g per day in four divided doses. It was observed that a single dose of cysteamine administered intravenously suppressed the leukocyte cystine level for more than 24 hours. However, regular intravenous administration of cysteamine would not be practical. Therefore, there is the need for formulations and delivery methods that increase the plasma levels, and thus intracellular concentration as well decreasing the number of daily doses. The improvement of the quality of life for patients is a goal of a novel cysteamine therapy. Compliance remains a problem firstly due to the unpalatable taste and odor of the product and secondly for the frequent administration doses. More palatable, absorbable and controlled release formulation of cysteamine are required for improving the adherence of patients to the therapy, remembering that the treatment lasts for all the life of the patient.

Because of the heavy regimen and the associated symptoms, patient non-adherence with cysteamine therapy remains a major problem, particularly among adolescent and young adult. The reduction of the frequency of required cysteamine dose by giving a prolonged controlled release preparation and the improvement of the taste and smell problems would increase the adherence to the therapy.

Some technologies have been used for facing this administration problem but all provide a delayed drug release dosage forms.

International patent application WO 2007/089670 describes an "enterically coated" tablet coated with a membrane that remains intact in the stomach but dissolves and releases the drug in the small intestine. The "enteric coating" is a polymeric material which insulates the drug core. Typically, the enteric coating material is dissolved before the therapeutically active agent is released from the dosage form, so delaying the dissolution of the core. A suitable pH-sensitive polymer dissolves in intestinal juices at a pH greater than 4.5, such as within the small intestine and therefore permits the release of drug substance in the small intestine and not in the stomach. This formulation has been considered useful for the long time treatment of cysteamine in order to decrease the gastro-disturb and provide an effective treatment of cystinosis. The exact amount of cysteamine required for the effective treatment vary from subject to subject, depending on age, weight, general conditions and the severity of the condition being treated. An appropriate "effective" individual amount may be titrated if the formulation proposed possesses a certain grade of flexibility. This is not achievable using gastro-resistant tablets containing a fixed dose that cannot be divided in two pieces without destroying the gastro-resistance of the medicine.

We know that it is not required for cysteamine bioavailability to delay the release until the dosage form reached the intestine since the drug is mainly absorbed in the stomach and the first tract of intestine. The delayed dosage form was done in the known art, in order to avoid the presence of a huge amount of free cysteamine in the stomach, responsible of the unpleasant taste and smell.

We have now found that cysteamine and derivatives thereof can be formulated as a microparticle powder with better taste and odor and good palatability when dispersed in water for the administration.

We discovered that the simply embedding the drug in a lipid matrix is able to slow down the dissolution rate and mask the taste and smell. To control the drug availability would improve the adherence to the therapy without affecting the effectiveness. Moreover, the delivery of cysteamine at slow rate reduces the risk of gastric ulceration. The drug is very hydrophilic and the release rate control is difficult with the typical agents used in the prolonged release preparations, such as the hydrophilic polymers. Moreover, the release of cysteamine at slow rate from lipid matrixes is performed over the entire GI tract and not restricted to the small intestine. This improves absorption, reduces the frequency of administration and masks the drug nauseating odor. At the same time, the gastric mucosa is not loaded with a large amount of dissolved drug that determines the breath smell and the stomach distress.

DESCRIPTION OF THE INVENTION

Figure 1:
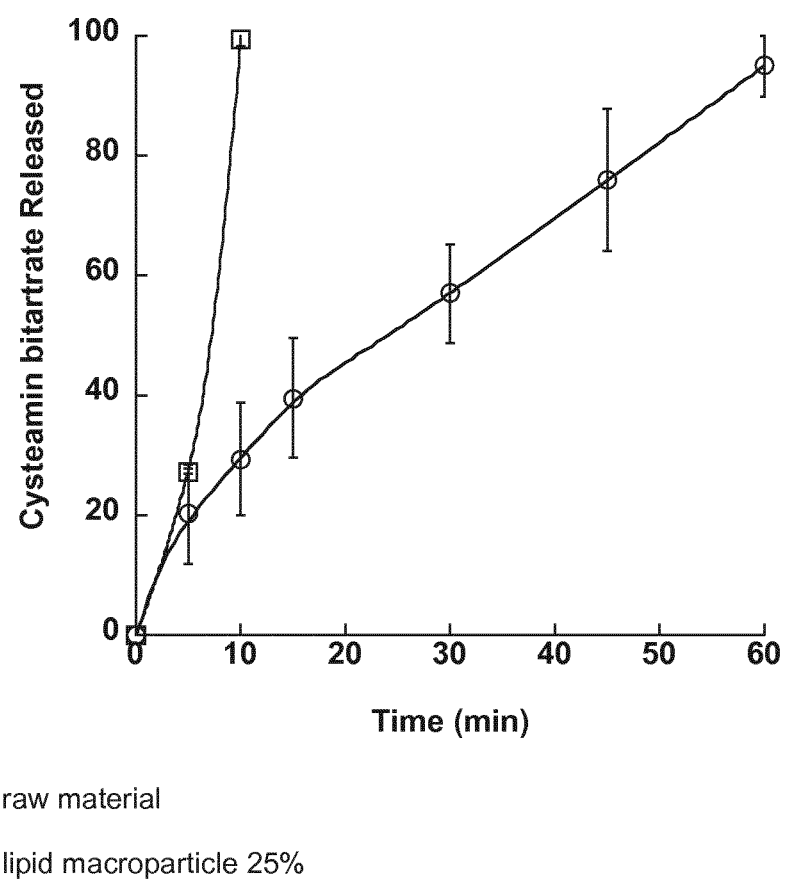
FIG. 1—dissolution profiles of cysteamine bitartrate raw material and lipid microparticles 25% of example 1
Figure 2:
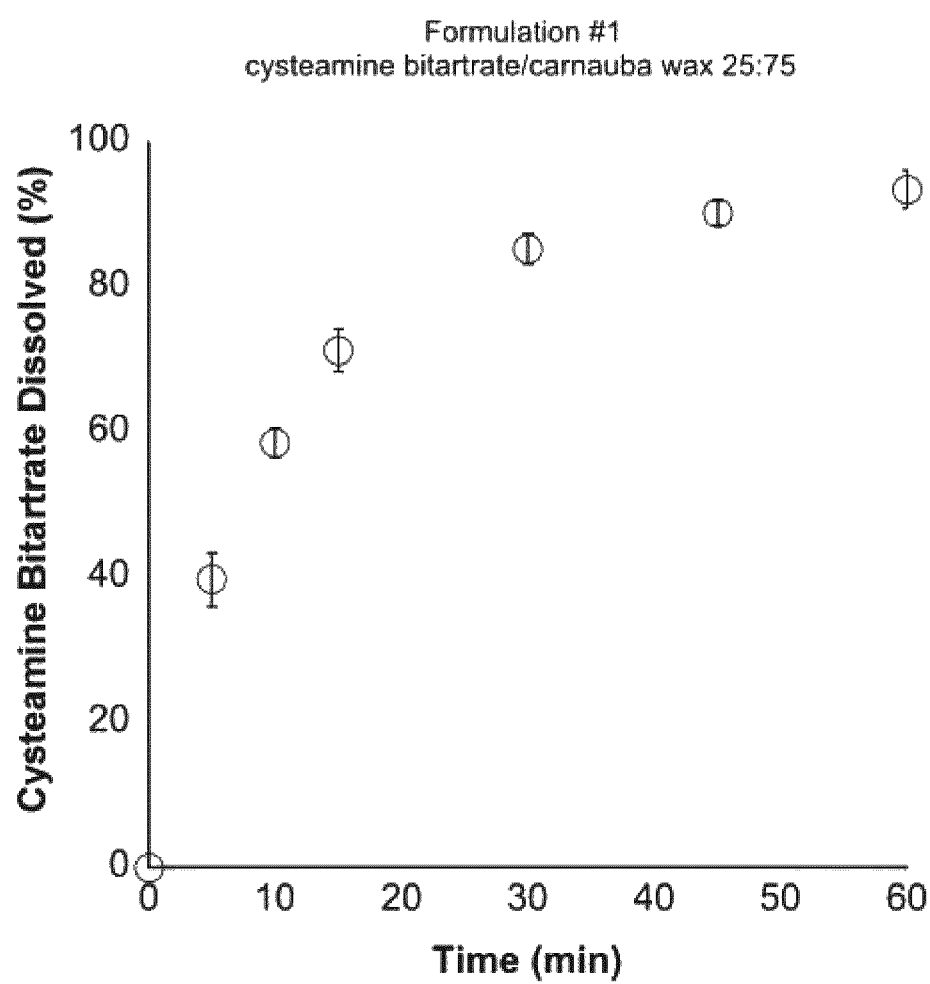
FIG. 2—release profiles of formulations #1 (mean value±standard value, n=3)
Figure 3:
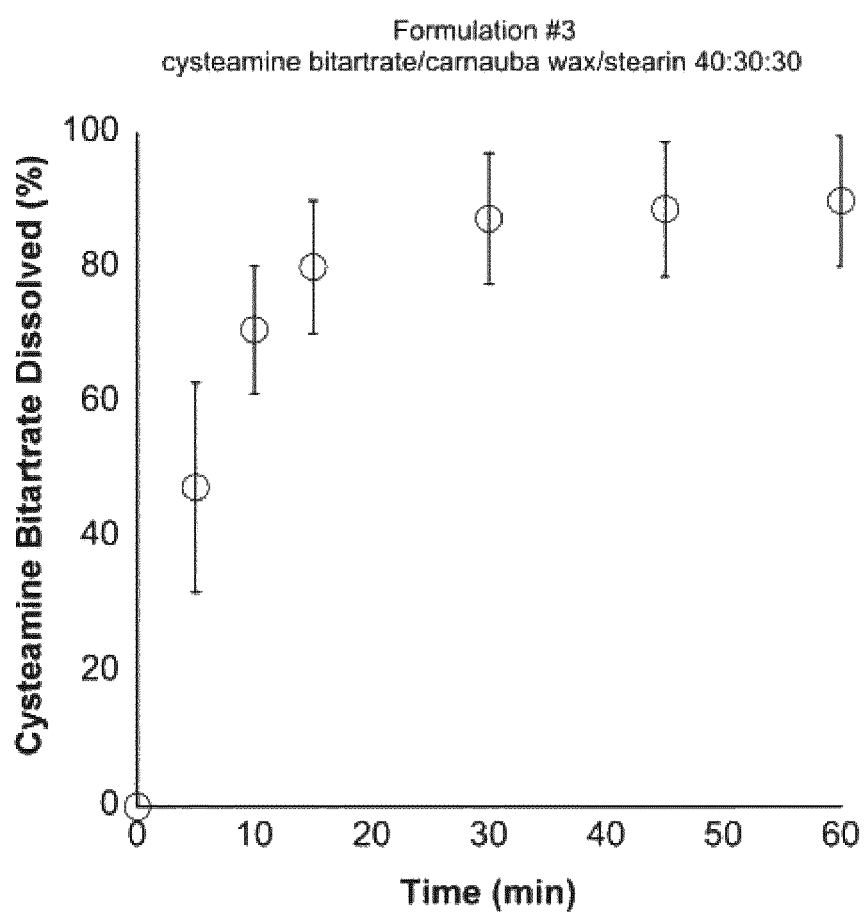
FIG. 3—release profiles of formulations #3 (mean value±standard value, n=3)
Figure 4:
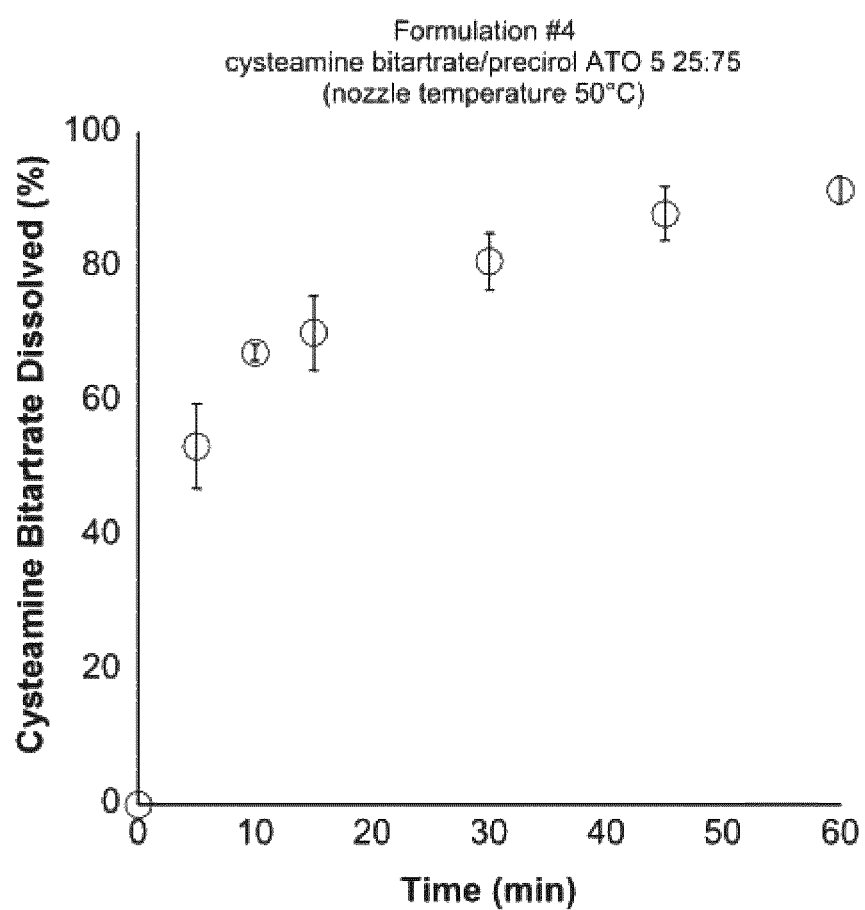
FIG. 4—release profiles of formulations #4 (mean value±standard value, n=3)
Figure 5:
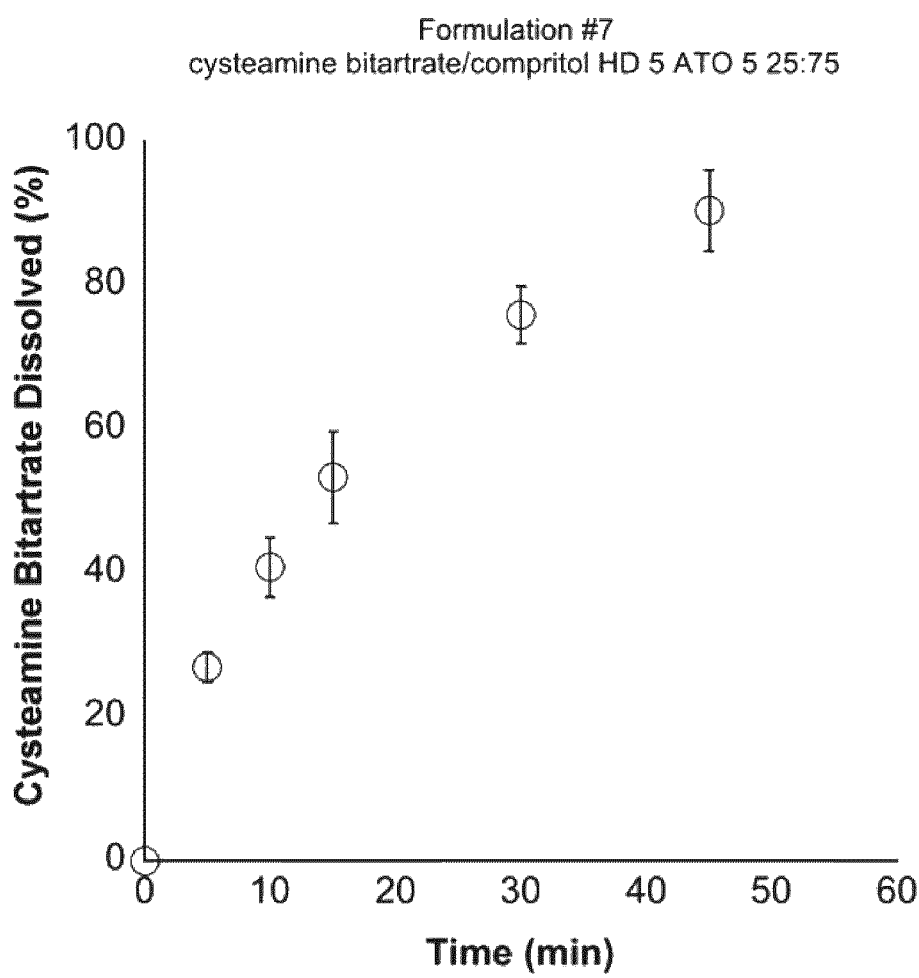
FIG. 5—release profiles of formulations #7 (mean value±standard value, n=3)

A first object of the present invention is a microparticle powder consisting of lipid matrix microparticles of cysteamine or a derivative thereof optionally layered with a powder.

A further object of the present invention is an oral formulation containing a microparticle powder consisting of lipid matrix microparticles of cysteamine or a derivative thereof optionally layered with a powder, in admixture with one or more pharmaceutically acceptable excipients.

Cysteamine can be used as such or as a derivative thereof such as a salt, a biological precursor or a metabolite.

Preferably a cysteamine salt such as cysteamine hydrochloride or bitartrate is used. Cysteamine bitartrate is more preferably used.

The lipid matrix is the most characterizing feature of the present formulation which makes it different from the formulations of the prior art that are classified reservoir or membrane release systems.

SUMMARY OF THE INVENTION

The lipid matrix according to the present invention contains an adjuvant in addition to cysteamine or a derivative thereof. The adjuvant allows the construction of the solid macroparticles of cysteamine or a derivative thereof.

Examples of substances useful as adjuvants according to the present invention are:
  fatty acids and their salts, esters and corresponding alcohols, such as aluminum stearate, sodium stearyl fumarate, stearic, lauric, palmitic, linoleic or myristic acid, cetostearyl alchohol, glyceryl monostearate, glyceryl palmitostearate, polyoxyethylene stearates, sucrose palmitate; and
  other lipid excipients such as carnauba wax, glyceril tristearate (stearin), glyceril dibehenate EP (Compritol 888 ATO), behenoyl polyoxyl-8 glycerides NF (Compritol HD 5 ATO), glycerol distearate type I, EP (Precirol ATO 5).

Behenoyl polyoxyl-8-glycerides NF (Compritol HD 5 ATO) is particularly preferred. Said substances can be used individually or in admixture.

The microparticles have a mean particle size lower than 800 urn, preferably lower than 500 μm.

For the purpose of the present invention, the term "mean particle size" refers to a particle size volume-weight distribution obtained by sieving the powder mass.

The lipid matrix microparticles according to the invention can be layered with spray-dried microparticle powders to increase their wettability when dispersed in water or other fluids for their administration and/or to adjust their taste.

Said spray-dried microparticles preferably consist of a mixture of a phospholipid, such as lecithin, with one or more of the following substances:
  sucralfate gel
  sugars, like glucose, lactose, sucrose, trehalose, maltose, mannose or fructose;
  polyalcohols, like mannitol, xylitol, sorbitol, lactitol;
  amino-sugars, like glucosamine;
  polysaccharides, like starch, dextran, dextrin, cyclodextrins and derivatives, maltodextrins.

Still more preferably, the lipid microparticles according to the present invention are layered with spray-dried microparticles consisting of a mixture of lecithin with mannitol or sucralfate gel.

A particularly preferred embodiment of the present invention is an oral formulation containing a microparticle powder consisting of lipid matrix microparticles of cysteamine or a derivative thereof layered with microparticles of sucralfate gel, in admixture with one or more pharmaceutically acceptable excipients.

The microparticle lipid powder according to the present invention provides delivery methods and compositions that overcome the known problems related to cysteamine delivery while maintaining a less frequent dosing (2 per day vs. 4 per day) as for the enteric-coated compositions, increases patient acceptance as taste and reduces gastrointestinal side effects (e.g., pain, heartburn, acid production, vomiting) and other side effects related to the repulsive drug smell.

Moreover, the microparticle preparations have a remarkable flexibility as formulation since the dose is decided at the administration time according to the physician prescription. In addition, since their travel through the pyloric valve to the intestine is facilitated by the small size, a reduced residence time in the stomach is exhibited by the preparation.

As described herein, a stable and release controlled pharmaceutical composition for administration of cysteamine or derivatives thereof was prepared by embedding the drug in a lipophilic matrix capable to prolong the release rate of the drug independently on the GI tract in which the preparation is located.

The microparticle lipid powder according to the present invention can be prepared following any suitable pharmaceutical technique known in the art for the preparation of microparticle formulations.

Preferably, the microparticle structure is obtained by the spray congealing technique starting from a dispersion of the drug in a melted mass made by lipophylic adjuvants melted at a temperature lower than the drug melting point.

The most appropriate lipid substance for the preparation of matrix microparticles of cysteamine and derivatives is a triglyceride with Hydrophilic Lipophilic Balance lower than 6 and higher than 2 to overcome the problem deriving from the hydrophilicity of cysteamine when dispersed in the melted lipid excipient.

The technique drives to the preparation of a powder in which the component microparticles have a lipophilic nature. Each microparticle constitutes a micro-matrix, from which the drug is released by diffusion through the particle porosity, and not a reservoir for drug release. The dose of cysteamine microparticle dispersed in water or another suitable liquid, allows the preparation of a smooth suspension to ingest. The dose of formulation is easy to tailor to the subject to treat, allowing the dose titration according to his needs. Concerning the release rate of the lipid microparticles, the prolongation of the release was set at not more than one hour, considering that the goal was to allow the preparation to start the release the drug partially into the stomach, completing the release in the intestine. This decision allows the taste masked preparation to be dispersed in a liquid and ingested by the patient in few minutes, avoiding a massive delivery of drug into the stomach. As an example a comparison between the cysteamine release from raw material and from the lipid microparticles is reproduced in FIG. 1.

Thus, in a typical but not exclusive manufacturing process, the lipid microparticles of cysteamine or derivatives thereof were prepared by spray-congealing. Examples of cysteamine derivatives include hydrochloride, bitartrate and phospho-cysteamine. In general, lipid microparticles were prepared using the composition in which the cysteamine content was between 10 to 40% w/w and the excipients from 60 to 90% used alone or in admixture. The microparticles were obtained by heating the lipid mass until complete melting. Then, under stirring, cysteamine derivative was added to the molten mass and dispersed for few minutes. At this temperature also the active principle could be melted. However, by appropriately selecting the temperature, we can have a dispersion of solid particles of cysteamine in a melted mixture of excipients. The fused lipid mixture was sprayed through a nozzle at a temperature of few degrees lower than the fusion value and at a pressure of 2 bar. Since the lipid cysteamine formulation is very hydrophobic, its dispersion in water for dose preparation could be hindered since the microparticles float on the dispersive liquid. We overcome this potential drawback by layering the lipid microparticles with a spray-dried microparticle powder.

In a particularly preferred embodiment of the present invention a new technique for modifying the surface properties of lipid microparticles consisting in mixing by tumbling the lipid microparticles with a microparticle powder of sucralfate gel/lecithin obtained by spray drying is used. In this way a powder made of sucralfate gel/lecithin spray-dried microparticles gave rise to a hydrophilic layer on the surface of the lipid microparticles simply by mixing. The layered lipid microparticles immediately immersed in the dispersing liquid.

Sucralfate gel is a drug prescribed for the treatment of GI ulcers. According to the present invention it is distributed on the surface of lipid microparticles by tumbling and is used at a sub-therapeutic dose compared to its dose for ulcer treatment. Despite this, it has been shown that low doses of sucralfate are able to protect the gastric mucosa. Therefore, by mixing the lipid particles with the sucralfate gel spray dried powder, the sucralfate microparticles stuck on the surface of lipid microparticles imparting them surface wettability conditions. At the same time, sucralfate exerts a protective action towards the gastro-injury of cysteamine. In particular, we have surprisingly found that the microparticles of sucralfate spontaneously stick on the surface of cysteamine lipid microparticles simply by tumbling the two powders' mixture. As far as we know, there is no disclosure in the literature that the sucralfate spray dried particles that are insoluble in water, covering the surface of lipid microparticles modifies their surface energy allowing wetting.

Thus, the present invention provides slow release formulations of cysteamine and derivatives prepared as lipid matrix drug delivery system in which an adherent stratum of hydrophilic substances, such as sucralfate gel microparticles, allows the wetting of the lipid microparticles, mask the taste and control the release that is prompt and slow in the GI tract.

The embedding in lipid matrix maintains the cysteamine release all over the GI tract conditions. Because of the matrix structure, the drug taste is masked and the release to the GI is under control, thereby improving uptake of cysteamine while reducing gastric side effects also due to the sucralfate gel layer. This will result in a less frequent administration currently associated with cysteamine therapy.

The cysteamine is present in the microparticle composition in a therapeutically effective amount that can allow the titration of the dose to the patient requirements; typically, the composition is a multi-unit dosage form to the dispensed in sachets or in a container of large amount to be dosed with a dosing spoon. The amount of cysteamine administered can be titrated to age, weight, and to the severity of the subject condition following the prescribing physician. Maintenance therapeutic doses of 1-2 g daily are administered bid or tid. Current non-prolonged release doses for children are about 1.30 g/m$^2$ body surface area and are administered 4-5 times per day.

EXAMPLES

Various types of lipid microparticles of cysteamine bitartrate, using the technology of spray-congealing, were prepared.

Example 1

A lipid excipient with low melting point range (62-65° C.) and HLB 5.0 was selected. In particular, Compritol HD5 ATO, made of glyceryl behenate and polyethylene glycol behenate, was used. Microparticles were obtained by heating the lipid mass at about 70° C. until complete melting. Then, four compositions of microparticles containing cysteamine bitartrate were prepared. The drug added under stirring to the lipid molten mass at the concentrations of 15, 20, 25 or 30% respectively, was left at 65-68° C. for 5 minutes at which the drug is not melted (melting point 78-79° C.). The dispersion was sprayed through the spray congealing apparatus nozzle at a temperature of 70° C. and at a pressure of 2.5 bar. No phase separation was observed. The particle size of the obtained microparticles was between 300 and 700 μm.

The in vitro dissolution tests were conducted in an USP Apparatus II at pH 1.2 for 1 hour. The dissolution profiles of cysteamine bitartrate raw material and the lipid microparticles are shown in FIG. 1. The cysteamine bitartrate raw material was completely dissolved in 10 minutes. The lipid microparticle 25% showed a slow release of cysteamine bitartrate of about 90% in 1 hour in the acid environment. Due to the hydrophobic characteristics of the microparticles, they did not soak in the dissolution medium but remain on the top of the medium.

Example 2

Microparticles were obtained by heating a lipid mass composed of carnauba wax and stearic acid 1:1, at 95° C. until complete melting. Then, cysteamine bitartrate as a percentage from 30 to 40% was added, under stirring, to the lipid molten mass and left at 95° C. for 5 minutes. The complete dispersion of the active principle in the lipid molten mass was observed. The suspension was sprayed through a nozzle at a temperature of 90° C. and at a pressure from 1.0 to 2.0 bar in an environment at room temperature obtaining solid microparticles of the formulation. The mean particle size of the microparticles was between 300 and 500 μm.

Example 3

A lipid excipient with low melting point and HLB 2.0 was selected. In particular, Precirol ATO 5, made of glycerol distearate type I Eur. Pharm., was used. Microparticles were obtained by heating the lipid mass at about 50° C. until complete melting. Then, a composition of microparticles containing cysteamine bitartrate were prepared. The drug added under stirring to the lipid molten mass at the concentration of 25%, respectively, was left at 57° C. for 5 minutes. The dispersion was sprayed through the spray congealing apparatus nozzle at a temperature of 52° C. and at a pressure of 2.5 bar. No phase separation was observed. The particle size of the obtained microparticles was between 300 and 500 μm.

Example 4

Carnauba wax and stearin excipients with high melting point were selected. Microparticles were obtained by heating the lipid mass at about 90° C. until complete melting. Then, compositions for microparticles containing cysteamine bitartrate were prepared. The drug added under stirring to the lipid molten mass at the concentrations of 20, 25, 30 or 40% w/w, respectively, was left at 85° C. for 5 minutes. The dispersion was sprayed through the spray congealing apparatus nozzle at a temperature between 80-86° C. and at a pressure of 2.5 bar. No phase separation was observed. The mean particle size of the obtained microparticles was between 50 and 300 μm.

Example 5

The lipid microparticles of cysteamine bitartrate according to the present invention prepared by spray-congealing are reported in the following table I.

TABLE I

Lipid microparticles of cysteamine bitartrate (CB) by spray-congealing

| Lipid microparticles | composition | Ratio (%) | Nozzle temperature (° C.) | Atomization pressure (bar) | Yield (%) |
|---|---|---|---|---|---|
| #1 | CB/carnauba wax | 25:75 | 91 | 2 | 56 |
| #2 | CB/carnauba wax/stearin | 30:35:35 | 92 | 2 | 60 |
| #3 | CB/carnauba wax/stearin | 40:30:30 | 92 | 2 | 46 |
| #4 | CB/Precirol ATO 5 | 25:75 | 50 | 2.5 | 52 |
| #5 | CB/Precirol ATO 5 | 25:75 | 70 | 2.5 | 77 |
| #6 | CB/Precirol ATO 5 | 30:70 | 70 | 2.5 | 36 |
| #7 | CB/Compritol HD 5 ATO | 25:75 | 70 | 2.5 | 56 |
| #8 | CB/Compritol HD 5 ATO | 30:70 | 72 | 2.5 | 49 |

The drug content in the lipid microparticles was determined using the following procedure. An accurately weighed amount of lipid microparticles, containing theoretically 25 mg of drug, was dispersed in a 100 ml volumetric flask containing 80 ml of phosphate buffer pH 7.4 and 0.1% of EDTA. The dispersions were heated up, under magnetic stirring, to 100° C. and maintained at that temperature for 15 minutes to allow the complete melting of the lipid carrier. Each flask was left to cool to room temperature under magnetic stirring and then brought to volume with the phosphate buffer pH 7.4, containing 0.1% of EDTA. The dispersion was filtered through a 0.45 um cellulose membrane and analyzed by HPLC analysis. The results are summarized in the following table II.

TABLE II

Content (%) of cysteamine bitartrate in the lipid microparticles (mean value ± standard deviation, n = 3)

| formulation | Drug content (%) |
|---|---|
| #1 | 23.2 ± 0.3 |
| #2 | 35.1 ± 3.3 |
| #3 | 37.8 ± 0.4 |
| #4 | 22.9 ± 2.2 |
| #5 | 26.6 ± 1.3 |
| #6 | 31.7 ± 2.9 |
| #7 | 23.2 ± 1.5 |
| #8 | 27.1 ± 0.9 |

Example 6

The morphological characterization of the lipid microparticles prepared according to the procedure described in the preceding examples was performed with scanning electron microscopy (SEM). The lipid microparticles according to Formulations #1 were almost spherical, with an irregular surface. Also in the case of lipid microparticles according to Formulations #5 the shape was spherical and the irregularity of the surface was more pronounced.

The lipid microparticles according to Formulations #7 were round shaped with smoother surface.

Example 7

The formulations prepared according to the procedure described in the preceding examples were smelled, separately, by three people to evaluate the odour masking effect.

A scale from 0-5 was assigned to each formulation and the results are reported in the following table.

TABLE III

Smell of the formulations (n = 3)

| formulation | Impression on smell | | |
|---|---|---|---|
| #1 | 0 | 0 | 0 |
| #2 | 3 | 3 | 2 |
| #3 | 1 | 2 | 2 |
| #4 | 4 | 4 | 4 |
| #5 | 0 | 1 | 1 |
| #6 | 1 | 1 | 1 |
| #7 | 0 | 0 | 0 |
| #8 | 2 | 4 | 4 |

0 odourless
1 less intense
2 medium
3 strong
4 very strong

Example 8

In vitro release studies were performed. The USP Apparatus II, with paddle rotating at 100 rpm, in 500 ml of simulated gastric fluid without enzymes pH 1.2 at a temperature of 37° C., was used. The simulated gastric environment was selected to evaluate the drug release in the stomach.

The dissolution profiles are shown in FIGS. 2-5.

Formulations #3 and #4 showed a faster release of cysteamine bitartrate than formulations #1 and #8.

Example 9

Figure 6:
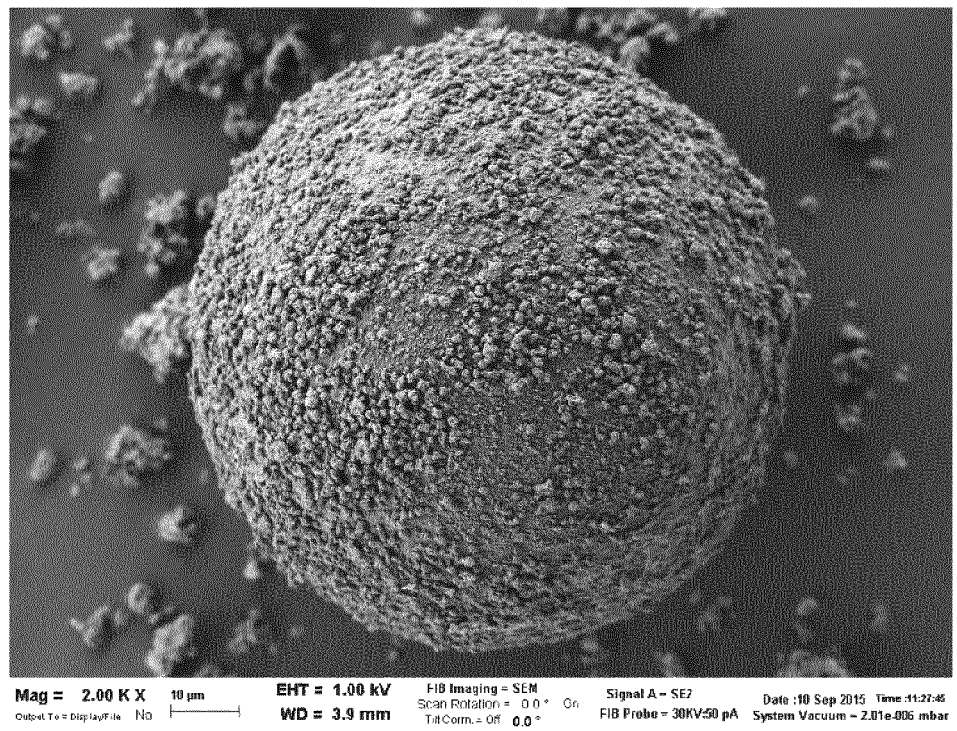
FIG. 6—SEM image of formulation #8

The layering powder of sucralfate gel/lecithin was prepared in the following manner: The microparticulate powders were prepared by spray-drying a dispersion of sucralfate gel with lecithin accordingly to the following procedure: 10 g of sucralfate (as sucralfate humid gel) was dispersed in 240 mL of water and homogenized; 0.5-1.5 g of lecithin was dissolved in 10 mL of ethanol at 40° C. and mixed with sucralfate gel dispersion. Sucralfate gel and lecithin ratios used were between 95:5 and 85:15 (w/w) keeping the solid concentration in the dispersion to spray at 4% (w/v). All the dispersions were spray-dried using a Buchi Mini Spray Dryer B-191 in the following conditions: inlet temperature 120° C., outlet temperature 50° C., feed rate 6.0 mL/min, nozzle diameter 0.7 mm, drying air flow 600 L/h. The median volume diameters of powders obtained were around 3.6 μm with low bulk density around 0.45±0.02 g/cm$^3$, typical of fine powders, poor packing and no flow. The sucralfate gel/lecithin spray dried powders prepared showed typical spray-dried round particles (FIG. 6).

By working in a similar way spray-dried microparticles of mannitol/lecithin were prepared and mixed in powder form with lipid microparticles (1:9% w/w) for layering or dry coating.

The invention claimed is:

1. An oral formulation containing a microparticle powder comprising lipid matrix microparticles consisting of a cysteamine or a derivative thereof, wherein said lipid matrix microparticles are layered with spray-dried microparticles of sucralfate gel/lecithin, in admixture with one or more pharmaceutically acceptable excipients wherein the sucralfate gel microparticles spontaneously stick on a surface of the lipid matrix microparticles and impart the lipid matrix microparticles with surface wettability, and wherein the derivative thereof includes cysteamine bitartrate or cysteamine hydrochloride.

2. The oral formulation according to claim 1 wherein cysteamine bitartrate is used.

3. The oral formulation according to claim 1 wherein the lipid matrix contains an adjuvant selected among fatty acids and their salts, esters and corresponding alcohols and other lipid excipients or mixtures thereof.

4. The oral formulation according to claim 3 wherein the adjuvant is selected from the group consisting of aluminum stearate, sodium stearyl fumarate, stearic, lauric, palmitic, linoleic or myristic acid, cetostearyl alchohol, glyceryl monostearate, glyceryl palmitostearate, polyoxyethylene stearates, sucrose palmitate, carnauba wax, glyceril tristearate, glyceril dibehenate EP, behenoyl polyoxyl-8 glycerides NF, glycerol distearate type I, EP-and mixtures thereof.

5. The oral formulation according to claim 4 wherein the adjuvant is behenoyl polyoxyl-8-glycerides NF.

6. The oral formulation according to claim 1 wherein the microparticle powder has a mean particle size lower than 800 μm.

7. The oral formulation according to claim 6 wherein the microparticle powder has a mean particle size lower than 500 μm.

8. The oral formulation according to claim 1, wherein the spray-dried microparticles further comprise one or more substances selected from the group of consisting of sugars, polyalcohols, amino-sugars, polysaccharides and mixtures thereof.

9. The oral formulation according to claim 8 wherein said one or more substances is selected from the group consisting of, glucose, lactose, sucrose, trehalose, maltose, mannose, fructose, mannitol, xylitol, sorbitol, lactitol, glucosamine, starch, dextran, dextrin, cyclodextrins and derivatives, maltodextrins and mixtures thereof.

10. The oral formulation according to claim 9 wherein said one or more substances is mannitol.

11. A method of treating cystinosis and neurodegenerative diseases, comprising administering an effective amount of the oral formulation of claim 1 to a patient in need thereof wherein the neurodegenerative disease is selected from Huntington's disease, Alzheimer's disease, or Parkinson's disease.

12. The method of claim 11, wherein the amount of cysteamine administered is 1-2 grams daily.

* * * * *